(12) United States Patent
Hoglund et al.

(10) Patent No.: US 9,994,914 B2
(45) Date of Patent: Jun. 12, 2018

(54) MUTATION IN THE EPIDERMAL GROWTH FACTOR RECEPTOR KINASE DOMAIN

(71) Applicant: Roche Molecular Systems, Inc., Pleasanton, CA (US)

(72) Inventors: Bryan Hoglund, Pleasanton, CA (US); Janet Jin, Foster City, CA (US); Yan Li, Palo Alto, CA (US); Wei-Min Liu, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days. days.

(21) Appl. No.: 14/873,931

(22) Filed: Oct. 2, 2015

(65) Prior Publication Data
US 2017/0067114 A1    Mar. 9, 2017

Related U.S. Application Data

(60) Provisional application No. 62/061,965, filed on Oct. 9, 2014.

(51) Int. Cl.
| | |
|---|---|
| *C12Q 1/68* | (2018.01) |
| *C12P 19/34* | (2006.01) |
| *A61K 31/517* | (2006.01) |
| *A61K 31/5377* | (2006.01) |
| *C07K 16/28* | (2006.01) |
| *C07K 16/32* | (2006.01) |

(52) U.S. Cl.
CPC .......... *C12Q 1/6886* (2013.01); *A61K 31/517* (2013.01); *A61K 31/5377* (2013.01); *C07K 16/2863* (2013.01); *C07K 16/32* (2013.01); *C07K 2317/21* (2013.01); *C07K 2317/24* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

FOREIGN PATENT DOCUMENTS

| WO | 2006103421 A2 | 10/2006 |
|---|---|---|
| WO | 2006106316 A2 | 10/2006 |
| WO | 2007039705 A1 | 4/2007 |
| WO | 2008066498 A1 | 6/2008 |
| WO | 2013068103 A1 | 5/2013 |
| WO | 2014086707 A1 | 6/2014 |
| WO | 2014135669 A1 | 9/2014 |

OTHER PUBLICATIONS

Paez J G et al., EGFR mutations in lung cancer correlation with clinical response to gefitinib therapy, Science, Jun. 4, 2004, pp. 1497-1500, vol. 304, No. 5676.

Pao W et al., EGF receptor gene mutations are common in lung cancers from never smokers and are associated with sensitivity of tumors to gefitinib and erlotinib, PNAS, Sep. 7, 2004, pp. 13306-13311, vol. 10, No. 36.

Sordella R et al., Gefitinib-sensitizing EGFR mutations in lung cancer activate anti-apoptotic pathways, Science, Aug. 20, 2004, pp. 1163-1167, vol. 305, No. 5687.

*Primary Examiner* — Jehanne S Sitton
(74) *Attorney, Agent, or Firm* — Carol Johns

(57) ABSTRACT

A new in-frame deletion was found in exon 19 of the EGFR gene, the exon that is often mutated in tumors. The invention comprises methods of detecting the mutation, methods of prognosis and methods of predicting response to treatment based on the presence of absence of the mutation.

10 Claims, 3 Drawing Sheets

FIGURE 1: SEQ ID NO:1

```
   1 ATGCGACCCTCCGGGACGGCCGGGGCAGCGCTCCTGGCGCTGCTGGCTGCGCTCTGCCCG
  61 GCGAGTCGGCTCTGGAGGAAAAGAAAGTTTGCCAAGGCACGAGTAACAAGCTCACGCAG
 121 TTGGGCACTTTTGAAGATCATTTTCTCAGCCTCCAGAGGATGTTCAATAACTGTGAGGTG
 181 GTCCTTGGGAATTTGGAAATTACCTATGTGCAGAGGAATTATGATCTTTCCTTCTTAAAG
 241 ACCATCCAGGAGGTGGCTGGTTATGTCCTCATTGCCCTCAACACAGTGGAGCGAATTCCT
 301 TTGGAAAACCTGCAGATCATCAGAGGAAATATGTACTACGAAAATTCCTATGCCTTAGCA
 361 GTCTTATCTAACTATGATGCAAATAAAACCGGACTGAAGGAGCTGCCCATGAGAAATTTA
 421 CAGGAAATCCTGCATGGCGCCGTGCGGTTCAGCAACAACCCTGCCCTGTGCAACGTGGAG
 481 AGCATCCAGTGGCGGGACATAGTCAGCAGTGACTTTCTCAGCAACATGTCGATGGACTTC
 541 CAGAACCACCTGGGCAGCTGCCAAAAGTGTGATCCAAGCTGTCCCAATGGGAGCTGCTGG
 601 GGTGCAGGAGAGGAGAACTGCCAGAAACTGACCAAAATCATCTGTGCCCAGCAGTGCTCC
 661 GGGCGCTGCCGTGGCAAGTCCCCCAGTGACTGCTGCCACAACCAGTGTGCTGCAGGCTGC
 721 ACAGGCCCCCGGGAGAGCGACTGCCTGGTCTGCCGCAAATTCCGAGACGAAGCCACGTGC
 781 AAGGACACCTGCCCCCCACTCATGCTCTACAACCCCACCACGTACCAGATGGATGTGAAC
 841 CCCGAGGGCAAATACAGCTTTGGTGCCACCTGCGTGAAGAAGTGTCCCCGTAATTATGTG
 901 GTGACAGATCACGGCTCGTGCGTCCGAGCCTGTGGGGCCGACAGCTATGAGATGGAGGAA
 961 GACGGCGTCCGCAAGTGTAAGAAGTGCGAAGGGCCTTGCCGCAAAGTGTGTAACGGAATA
1021 GGTATTGGTGAATTTAAAGACTCACTCTCCATAAATGCTACGAATATTAAACACTTCAAA
1081 AACTGCACCTCCATCAGTGGCGATCTCCACATCCTGCCGGTGGCATTTAGGGGTGACTCC
1141 TTCACACATACTCCTCCTCTGGATCCACAGGAACTGGATATTCTGAAAACCGTAAAGGAA
1201 ATCACAGGGTTTTTGCTGATTCAGGCTTGGCCTGAAAACAGGACGGACCTCCATGCCTTT
1261 GAGAACCTAGAAATCATACGCGGCAGGACCAAGCAACATGGTCAGTTTTCTCTTGCAGTC
1321 GTCAGCCTGAACATAACATCCTTGGGATTACGCTCCCTCAAGGAGATAAGTGATGGAGAT
1381 GTGATAATTTCAGGAAACAAAAATTTGTGCTATGCAAATACAATAAACTGGAAAAAACTG
1441 TTTGGGACCTCCGGTCAGAAAACCAAAATTATAAGCAACAGAGGTGAAAACAGCTGCAAG
1501 GCCACAGGCCAGGTCTGCCATGCCTTGTGCTCCCCCGAGGGCTGCTGGGGCCCGGAGCCC
1561 AGGGACTGCGTCTCTTGCCGGAATGTCAGCCGAGGCAGGGAATGCGTGGACAAGTGCAAC
```

FIGURE 1 (CONT.)

```
1621 CTTCTGGAGGGTGAGCCAAGGGAGTTTGTGGAGAACTCTGAGTGCATACAGTGCCACCCA
1681 GAGTGCCTGCCTCAGGCCATGAACATCACCTGCACAGGACGGGGACCAGACAACTGTATC
1741 CAGTGTGCCCACTACATTGACGGCCCCCACTGCGTCAAGACCTGCCCGGCAGGAGTCATG
1801 GGAGAAAACAACACCCTGGTCTGGAAGTACGCAGACGCCGGCCATGTGTGCCACCTGTGC
1861 CATCCAAACTGCACCTACGGATGCACTGGGCCAGGTCTTGAAGGCTGTCCAACGAATGGG
1921 CCTAAGATCCCGTCCATCGCCACTGGGATGGTGGGGGCCCTCCTCTTGCTGCTGGTGGTG
1981 GCCCTGGGGATCGGCCTCTTCATGCGAAGGCGCCACATCGTTCGGAAGCGCACGCTGCGG
2041 AGGCTGCTGCAGGAGAGGGAGCTTGTGGAGCCTCTTACACCCAGTGGAGAAGCTCCCAAC
2101 CAAGCTCTCTTGAGGATCTTGAAGGAAACTGAATTCAAAAAGATCAAAGTGCTGGGCTCC
2161 GGTGCGTTCGGCACGGTGTATAAGGGACTCTGGATCCCAGAAGGTGAGAAAGTTAAAATT
2221 CCCGTCGCTATCAAGGAATTAAGAGAAGCAACATCTCCGAAAGCCAACAAGGAAATCCTC
2281 GATGAAGCCTACGTGATGGCCAGCGTGGACAACCCCCACGTGTGCCGCCTGCTGGGCATC
2341 TGCCTCACCTCCACCGTGCAGCTCATCACGCAGCTCATGCCCTTCGGCTGCCTCCTGGAC
2401 TATGTCCGGGAACACAAAGACAATATTGGCTCCCAGTACCTGCTCAACTGGTGTGTGCAG
2461 ATCGCAAAGGGCATGAACTACTTGGAGGACCGTCGCTTGGTGCACCGCGACCTGGCAGCC
2521 AGGAACGTACTGGTGAAAACACCGCAGCATGTCAAGATCACAGATTTTGGGCTGGCCAAA
2581 CTGCTGGGTGCGGAAGAGAAAGAATACCATGCAGAAGGAGGCAAAGTGCCTATCAAGTGG
2641 ATGGCATTGGAATCAATTTTACACAGAATCTATACCCACCAGAGTGATGTCTGGAGCTAC
2701 GGGGTGACTGTTTGGGAGTTGATGACCTTTGGATCCAAGCCATATGACGGAATCCCTGCC
2761 AGCGAGATCTCCTCCATCCTGGAGAAAGGAGAACGCCTCCCTCAGCCACCCATATGTACC
2821 ATCGATGTCTACATGATCATGGTCAAGTGCTGGATGATAGACGCAGATAGTCGCCCAAAG
2881 TTCCGTGAGTTGATCATCGAATTCTCCAAAATGGCCCGAGACCCCCAGCGCTACCTTGTC
2941 ATTCAGGGGGATGAAAGAATGCATTTGCCAAGTCCTACAGACTCCAACTTCTACCGTGCC
3001 CTGATGGATGAAGAAGACATGGACGACGTGGTGGATGCCGACGAGTACCTCATCCCACAG
3061 CAGGGCTTCTTCAGCAGCCCCTCCACGTCACGGACTCCCCTCCTGAGCTCTCTGAGTGCA
3121 ACCAGCAACAATTCCACCGTGGCTTGCATTGATAGAAATGGGCTGCAAAGCTGTCCCATC
3181 AAGGAAGACAGCTTCTTGCAGCGATACAGCTCAGACCCCACAGGCGCCTTGACTGAGGAC
```

FIGURE 1 (CONT.)

```
3241 AGCATAGACGACACCTTCCTCCCAGTGCCTGAATACATAAACCAGTCCGTTCCCAAAAGG

3301 CCCGCTGGCTCTGTGCAGAATCCTGTCTATCACAATCAGCCTCTGAACCCCGCGCCCAGC

3361 AGAGACCCACACTACCAGGACCCCCACAGCACTGCAGTGGGCAACCCCGAGTATCTCAAC

3421 ACTGTCCAGCCCACCTGTGTCAACAGCACATTCGACAGCCCTGCCCACTGGGCCCAGAAA

3481 GGCAGCCACCAAATTAGCCTGGACAACCCTGACTACCAGCAGGACTTCTTTCCCAAGGAA

3541 GCCAAGCCAAATGGCATCTTTAAGGGCTCCACAGCTGAAAATGCAGAATACCTAAGGGTC

3601 GCGCCACAAAGCAGTGAATTTATTGGAGCATGA
```

MUTATION IN THE EPIDERMAL GROWTH FACTOR RECEPTOR KINASE DOMAIN

CROSS-REFERENCE TO RELATED APPLICATIONS

The present application claims priority to U.S. Provisional Appl. No. 62/061,965 filed Oct. 9, 2014, the disclosure of which is included herewith in its entirety.

SEQUENCE LISTING

The instant application contains a Sequence Listing which has been submitted electronically in ASCII format and is hereby incorporated by reference in its entirety. Said ASCII copy, created on Jun. 20, 2016, is named 32344-USI_SL.txt and is 5,515 bytes in size.

FIELD OF THE INVENTION

The invention relates to cancer diagnostics and companion diagnostics for cancer therapies. In particular, the invention relates to the detection of mutations that are useful for diagnosis and prognosis as well as predicting the effectiveness of treatment of cancer.

BACKGROUND OF THE INVENTION

Epidermal Growth Factor Receptor (EGFR), also known as HER1 or ErbB1, is a member of the type 1 tyrosine kinase family of growth factor receptors. These membrane-bound proteins possess an intracellular tyrosine kinase domain that interacts with various signaling pathways. Upon ligand binding, receptors in this family undergo dimerization and subsequent autophosphorylation of the tyrosine kinase domain. The autophosphorylation triggers a cascade of events in intracellular signaling pathways, including the Ras/MAPK, PI3K and AKT pathways. Through these pathways, HER family proteins regulate cell proliferation, differentiation, and survival.

A number of human malignancies are associated with aberrant expression or function of EGFR. (Mendelsohn et al., (2000), "*The EGF receptor family as targets for cancer therapy*," Oncogene, 19:6550-6565.) In particular, it has been demonstrated that some cancers harbor mutations in the EGFR kinase domain (exons 18-21). In non-small cell lung cancer (NSCLC), these mutations were shown to promote anti-apoptotic pathways in malignant cells. (Pao et al. (2004). "*EGF receptor gene mutations are common in lung cancers from "never smokers" and are associated with sensitivity of tumors to gefitinib and erlotinib*". P.N.A.S. 101 (36): 13306-13311; Sordella et al. (2004). "*Gefitinib-sensitizing EGFR mutations in lung cancer activate anti-apoptotic pathways*". Science 305 (5687): 1163-1167.)

Therapies targeting EGFR have been developed. For example, cetuximab (ERBITUX™) and panitumumab (VECTIBIX™) are anti-EGFR antibodies. Erlotinib (TARCEVA™) and gefitinib (IRESSA™) are quinazolines useful as orally active selective inhibitors of EGFR tyrosine kinase. These drugs are most effective in patients whose cancers are driven by aberrant EGFR activity. A randomized, large-scale, double-blinded study of IRESSA™ (IRESSA Pan-Asia Study (IPASS)) compared gefitinib to the traditional chemotherapy as a first-line treatment in non-small cell lung cancer (NSCLC). (Mok et al. (2009) "*Gefitinib or carboplatin-paclitaxel in pulmonary adenocarcinoma.*" N Eng J Med 361:947-957)). IPASS studied 1,217 patients with confirmed adenocarcinoma histology. The study revealed that progression-free survival (PFS) was significantly longer for IRESSA™ than chemotherapy in patients with EGFR mutation-positive tumors. The opposite was true for tumors where EGFR was not mutated: PFS was significantly longer for chemotherapy than IRESSA™. The study demonstrated that to improve a lung cancer patient's chances of successful treatment, EGFR mutation status must be known.

Analysis of clinical outcome revealed that patients with tumors harboring mutations in the kinase domain of EGFR (exons 18-21) have better response to erlotinib than those with tumors expressing wild-type EGFR. (U.S. Pat. Nos. 7,294,468 and 7,960,118) These mutations are predictive of response to tyrosine kinase inhibitors (TKIs) such as quinazolines erlotinib (TARCEVA™) and gefitinib (IRESSA™). Among the EGFR mutations, in-frame deletions and substitutions of nucleotides in the region of exon 19 including nucleotides 2235-2257 (corresponding to amino acids 746-753) is especially common in lung cancer patients (see U.S. Pat. No. 7,294,468 and Lynch et al. (2004) "*Activating mutations in the epidermal growth factor underlying responsiveness of non-small cell lung cancer to gefitinib.*" NEJM 350:2129.) These mutations are thought to result in an active kinase with altered properties, including increased susceptibility to inhibition. See Paez et al. (2004) *EGFR mutations in lung cancer: correlation with clinical response to Gefitinib therapy*, Science 304:1497.

Some mutations in the EGFR kinase domain are common, while others occur less frequently. However, it is essential that a clinical test for EGFR mutations target as many mutations as possible. This will assure that patients with rare mutations do not receive a "false negative" test result. If a rare mutation goes undetected, the patient with such a mutation will not receive potentially life-saving treatment. Therefore when a new mutation in the EGFR kinase domain is discovered, detecting this mutation has the potential of affecting the clinical outcome in some patients.

SUMMARY OF THE INVENTION

In one embodiment, the invention is a novel DNA sequence comprising a newly-identified mutation in exon 19 of the human EGFR gene consisting of 2257-2277>GCC, or mutation 2257-2262 del, or mutation 2266-2277 del.

In one embodiment, the invention is a method of treating a patient having a tumor possibly harboring cells with a mutation in the epidermal growth factor receptor (EGFR) gene, comprising testing the patient's sample for the presence of the mutated EGFR gene characterized by the mutation 2257-2277>GCC, or mutation 2257-2262 del, or mutation 2266-2277 del in SEQ ID NO: 1; and, if the mutation is present, administering to the patient an EGFR inhibitor compound. The inhibitor can be e.g., cetuximab, panitumumab, erlotinib or gefitinib. The method may further comprise detecting one or more of the mutations G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252.2277>AC, 2240-2264>CGAAAGA, 2239_2240 TT>CC, 2264 C>A and E746-A750 del AP ins. In further variations, the mutations are detected by an allele-specific detection method or by DNA sequencing.

In another embodiment, the invention is a method of determining the likelihood of response of a cancer patient to an EGFR inhibitor therapy (e.g., tyrosine kinase inhibitor therapy) comprising: testing the patient's sample for mutation 2257-2277>GCC, or mutation 2257-2262 del, or mutation 2266-2277 del in the EGFR gene in the patient's sample and, if the mutation is present, determining that the patient will likely respond to the EGFR inhibitor (e.g., tyrosine kinase inhibitor) therapy. The EGFR inhibitor therapy can be e.g., treatment with cetuximab, panitumumab, erlotinib or gefitinib. The method may further comprise testing the patient's sample one or more of the mutations G719A, G719C, K745-A750 del K ins, E746V, E746K, L747S. E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins in the EGFR gene and any of the mutations is reported as present, determining that the patient will likely respond to the EGFR inhibitor or tyrosine kinase inhibitor therapy. The mutations may be detected e.g., by an allele-specific detection method or by DNA sequencing.

In another embodiment, the invention is a method of treating a patient having a tumor possibly harboring cells with a mutation in the epidermal growth factor receptor (EGFR) gene, comprising: recommending that the patient's sample be tested for the presence of the mutated EGFR gene characterized by the mutation 2257-2277>GCC or mutation 2257-2262 del, or mutation 2266-2277 del in SEQ ID NO: 1; and if the mutation is detected, administering to the patient an EGFR inhibitor compound. The inhibitor compound can be e.g., cetuximab, panitumumab, erlotinib or gefitinib. The method may further comprise recommending that the patient's sample be tested for the presence of the mutated EGFR gene characterized by one or more of the mutations G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del A P ins; and, if any of the mutations is detected, administering to the patient a tyrosine kinase inhibitor compound. The mutations may be detected e.g., by an allele-specific detection method or by DNA sequencing.

In yet another embodiment, the invention is a method of detecting mutation 2257-2277>GCC or mutation 2257-2262 del, or mutation 2266-2277 del in the human EGFR gene with a mutation-specific oligonucleotide, such as e.g., an allele-specific amplification primer or an allele-specific detection probe. In a variation, the one or more mutations are detected by an allele-specific detection method or by DNA sequencing.

BRIEF DESCRIPTION OF THE DRAWINGS

FIG. 1 is the nucleotide sequence of the human EGFR gene (SEQ ID NO: 1).

DETAILED DESCRIPTION OF THE INVENTION

Definitions

To facilitate the understanding of this disclosure, the following definitions of the terms used herein are provided.

The term "n-m" or "n-m del" ("n-m del x") refers to a mutation that results in a nucleic acid lacking the nucleotides ("x" nucleotides) between positions "n" and "m." The term "n-m>XYZ" refers to a complex mutation where the nucleic acid is lacking the original nucleotides between positions "n" and "m," but nucleotide sequence XYZ is inserted in their place. For example, the term "2257-2277>GCC" refers to a mutation that results in a nucleic acid lacking the nucleotides 2257-2277 from the wild-type sequence and the nucleotide sequence GCC is inserted in the place of the deleted nucleotides.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient, inefficient or undetectable.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to the modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

As used herein, the term "target sequence", "target nucleic acid" or "target" refers to a portion of the nucleic acid sequence which is to be either amplified, detected or both.

The terms "hybridized" and "hybridization" refer to the base-pairing interaction of between two nucleic acids which results in formation of a duplex. It is not a requirement that two nucleic acids have 100% complementarity over their full length to achieve hybridization.

The terms "selective hybridization" and "specific hybridization" refer to the hybridization of a nucleic acid predominantly (50% or more of the hybridizing molecule) or nearly exclusively (90% or more of the hybridizing molecule) to a particular nucleic acid present in a complex mixture where other nucleic acids are also present. For example, under typical PCR conditions, primers specifically hybridize to the target nucleic acids to the exclusion of non-target nucleic acids also present in the solution. The specifically hybridized primers drive amplification of the target nucleic acid to produce an amplification product of the target nucleic acid that is at least the most predominant amplification product and is preferably the nearly exclusive (e.g., representing 90% or more of all amplification products in the sample) amplification product. Preferably, the non-specific amplification product is present in such small amounts that it is either non-detectable or is detected in such small amounts as to be easily distinguishable from the specific amplification product. Similarly, probes specifically hybridize to the target nucleic acids to the exclusion of non-target nucleic acids also present in the reaction mixture. The specifically hybridized probes allow specific detection of the target nucleic acid to generate a detectable signal that is at least the most predominant signal and is preferably the nearly exclusive (e.g., representing 90% or more of all amplification products in the sample) signal.

The present invention describes a novel mutation in the EGFR kinase domain that is useful for cancer diagnosis and prognosis, designing a therapy regimen and predicting success of the therapy.

The present invention comprises a novel mutation 2257-2277>GCC in the exon 19 (portion of the kinase domain) of the human EGFR gene. Mutation 2257-2277>GCC and the corresponding wild-type sequence are shown in Table 1. The mutation comprises two separate in-frame deletions: 2257-2262 del 6 and 2266-2277 del 12 as illustrated in Table 1.

TABLE 1

New mutation and wild-type sequence in exon 19 of the human EGFR gene

| SEQ ID NO: | DESCRIPTION | NUCLEOTIDE SEQUENCE |
| --- | --- | --- |
| 2 | WT 2250-2280 | AACATCTCCGAAAGCCAAC AAGGAAATCCTC |
| 3 | 2257-2277 > GCC | AACATCT------GCC--- ---------CTC |

In one embodiment, the present invention comprises oligonucleotides for detecting the mutation 2257-2277>GCC (or either of the mutations 2257-2262 del and 2266-2277 del) in exon 19 of human EGFR gene. Using the disclosure of the new mutations provided herein, one of skill in the art is able to design a suitable oligonucleotide able to specifically detect the novel mutations. In variations of this embodiment, some of the oligonucleotides are allele-specific primers for use in allele-specific PCR (see U.S. Pat. No. 6,627,402). An allele-specific primer typically possesses a 3'-end matched to the target sequence (the mutant sequence) and mismatched to the alternative sequence (e.g. the wild-type sequence). Optionally, allele-specific primers may contain internal mismatches with both the wild-type and mutant target sequence. Additional mismatches in allele-specific PCR primers have been shown to increase selectivity of the primers. See US20100099110, which is incorporated herein by reference in its entirety. For successful extension of a primer, the primer needs to have at least partial complementarity to the target sequence. Generally, complementarity at the 3'-end of the primer is more critical than complementarity at the 5'-end of the primer. (Innis et al. Eds. *PCR Protocols*, (1990) Academic Press, Chapter 1, pp. 9-11). This means that variations of the 5'-end, i.e. additions, substitutions or removal of nucleotides at the 5'-end, do not affect performance of a primer in a PCR assay. The present invention encompasses allele-specific primers capable of selectively driving amplification of a portion of exon 19 of human EGFR gene that contains the mutation 2257-2277>GCC (or either of the mutations 2257-2262 del and 2266-2277 del) but would not drive amplification of the same targets having a wild-type sequence at positions 2257-2277 (or positions 2257-2262, or positions 2266-2277).

In other variations of this embodiment, some of the oligonucleotides are detection probes specific for the mutation 2257-2277>GCC (or either of the mutations 2257-2262 del and 2266-2277 del) in exon 19 of human EGFR gene. A typical detection probe forms a stable hybrid to the target sequence (e.g. the sequence with the mutation 2257-2277>GCC) and does not form a stable hybrid with the alternative sequence (e.g. the wild-type sequence) under the reaction conditions at which the detection is carried out. For successful probe hybridization, the probe needs to have at least partial complementarity to the target sequence. Generally, complementarity close to the central portion of the probe is more critical than complementarity at the ends of the probe. (Innis et al. Chapter 32, pp. 262-267). This means that variations of the ends of the probe, i.e. additions, substitutions or removal of a few nucleotides, do not affect performance of the probe in hybridization. The present invention encompasses detection probes capable of selectively hybridizing to a portion of exon 19 of human EGFR gene that contains the mutation 2257-2277>GCC (or either of the mutations 2257-2262 del and 2266-2277 del) but would not hybridize to the same targets having a wild-type sequence at positions 2257-2277 (or positions 2257-2262, or positions 2266-2277). In further variations of this embodiment, the probe has a particular structure, including a protein-nucleic acid (PNA), a locked nucleic acid (LNA), a molecular beacon probe (Tyagi et al. (1996) Nat. Biotechnol. 3:303-308) or SCORPIONS® self-probing primers (Whitcombe et al. (1999) Nat. Biotechnol. 8:804-807). A probe may be labeled with a radioactive, a fluorescent or a chromophore label. For example, the mutations may be detected by real-time allele-specific polymerase chain reaction, where hybridization of a probe to the amplification product results in enzymatic digestion of the probe and detection of the digestion products (TaqMan® probe, Holland et al. (1991) P.N.A.S. USA 88:7276-7280). Hybridization between the probe and the target may also be detected by detecting the change in fluorescence due to the nucleic acid duplex formation (US20100143901) or by detecting the characteristic melting temperature of the hybrid between the probe and the target (U.S. Pat. No. 5,871,908).

Mutant EGFR gene or gene product can be detected in tumors or other body samples such as urine, sputum or blood plasma where tumor-derived cells or cell-free nucleic acids are known to be present.

Activating mutations of EGFR have been reported in 10-15% of unselected Western patients and 30-40% of Asian patients with Non-Small-Cell Lung Cancer (NSCLC). Among the EGFR mutations found in NSCLC, the majority occur in the first four exons of the intracellular tyrosine kinase domain. Specifically, various exon 19 in-frame deletions account for ~45% of all the activating mutations. (Cooper et al., (2014) *Molecular biology of lung cancer*, J Thorac Dis 2013; 5(S5):S479-S490. EGFR mutation-positive lung adenocarcinoma and lung cancer in never-smokers as such are nowadays considered as distinct biological tumor subsets in the view of molecular pathogenesis, Thu et al. (2012) *Lung adenocarcinoma of never smokers and smokers harbor differential regions of genetic alteration and exhibit different levels of genomic instability*. PLoS One 7:e33003. This tumor subset is characterized by its unique responsiveness to tyrosine kinase inhibitors (TKI), Koehler, et al. (2013) *Afatinib, erlotinib and gefitinib in the first-line therapy of EGFR mutation-positive lung adenocarcinoma: a review*, Onkologie 2013; 36(9):510-8.

In one embodiment, the invention is a method of determining a likelihood of response of a malignant tumor in a patient to tyrosine kinase inhibitors (TKIs) or EGFR inhibitors. The method comprises testing the patient's sample for the presence of the mutation 2257-2277>GCC (or either of the mutations 2257-2262 del and 2266-2277 del) in exon 19 of EGFR, and if the mutation is found, determining that the treatment is likely to be successful. In variations of this embodiment, the tyrosine kinase inhibitors are EGFR kinase inhibitors or EGFR inhibitors are, for example, cetuximab, panitumumab, erlotinib or gefitinib.

In a variation of this embodiment, the method further comprises testing the patient's sample for one more of the following mutations: G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins; and if one or more of the mutations are present, determining that the treatment with tyrosine kinase inhibitors is likely to be successful In one embodiment, the invention is a method of treating a patient having a tumor possibly harboring cells with an EGFR gene having the mutation 2257-2277>GCC (or either of the mutations 2257-2262 del and 2266-2277 del) in exon 19, the method comprising testing the patient's sample for the above mentioned mutation, and if the mutation is detected, administering to the patient a tyrosine kinase inhibitor (TKI) or an EGFR inhibitor or an EGFGR TKI inhibitor. In variations of this embodiment, the tyrosine kinase inhibitors are EGFR kinase inhibitors such as for example, erlotinib or gefitinib or EGFR inhibitors such as for example, cetuximab or panitumumab.

In another variation of this embodiment, the method further comprises testing the patient's sample for one more of the following mutations: G719A, G719C, K745-A750 del K ins, E746V, E746K, L747S, E749Q, A750P, A755V, 87681, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 22392240 TT>CC, 2264 C>A and E746-A750 del AP ins; and if one or more of the mutations are present, administering to the patient a compound that inhibits signaling of the mutant EGFR protein encoded by the mutated gene. The nucleotide changes causing the mutations listed above and methods of detecting them are disclosed in U.S. Pat. Nos. 7,294,468 and 7,960,118 (mutation E746-A750 del AP ins) US20130121996 (mutations 2236_2248>ACCC, 2237_2244>CGCCC, 2252_2277>AC, 2240-2264>CGAAAGA, 2239_2240 TT>CC and 2264 C>A). Multiple mutations can be detected simultaneously or separately by using hybridization to multiple probes, for example in a dot-blot or nucleic acid array format, multiplex PCR, for example multiplex allele-specific PCR and multiplex PCR followed by a probe melting assay with each probe characterized by a mutation-specific melting temperature.

A single or multiple mutations may also be detected by nucleic acid sequencing. Any of a number of sequencing technologies can be utilized. Sequencing can be performed e.g., by Sanger method, or the automated Sanger method. Other technologies include the single molecule sequencing technology such as the True Single Molecule Sequencing (tSMS) technology from Helicos Biosciences (Cambridge, Mass.) (see Harris et al., Science 320:106-109 (2008)). Another example is the 454 sequencing from 454 Life Sciences (Bradford, Conn.) (see Margulies et al. Nature 437:376-380 (2005)). Yet another example is the SOLiD™ technology (Applied Biosystems, Foster City, Calif.). Yet another example is the single molecule, real-time (SMRT™) sequencing technology of Pacific Biosciences, (Novato, Calif.). Yet another example is the nanopore sequencing (see Soni et al., Clin Chem 53: 1996-2001 (2007)).

Other examples of suitable sequencing technology include chemical-sensitive field effect transistor (chemFET) array (see U.S. Patent Application Publication No. 2009/0026082). Yet another example is the transmission electron microscopy (TEM) method, termed Individual Molecule Placement Rapid Nano Transfer (IMPRNT) (see PCT patent publication WO 2009/046445). Yet another example is the Ion Torrent™ single molecule sequencing from Life technologies (Foster City, Calif.) Yet another example is the massively parallel sequencing of millions of DNA fragments via sequencing-by-synthesis and reversible terminator-based sequencing chemistry (see Bentley et al., Nature 6:53-59 (2009)).

Some sequencing technologies and platforms are available commercially, such as the sequencing-by-hybridization platform from Affymetrix Inc. (Sunnyvale, Calif.) and the sequencing-by-synthesis platforms from 454 Life Sciences (Bradford, Conn.), Illumina (San Diego, Calif.) and Helicos Biosciences (Cambridge, Mass.). Other applicable methods include sequencing-by-ligation on the platform from Applied Biosystems (Foster City, Calif.). Other suitable sequencing technologies include, but are not limited to, the SMRT™ technology of Pacific Biosciences (Novato, Calif.), and the nanopore sequencing technology developed for example, by Oxford Nanopore Technologies (Oxford, UK).

In yet another embodiment, the invention is a method of treating a patient having a tumor comprising testing the patient's sample (or recommending that the patient's sample be tested) for the mutation 2257-2277>GCC (or either of the mutations 2257-2262 del and 2266-2277 del) in exon 19 of the EGFR gene and if the mutation is detected, administering to the patient an EGFR inhibitor, including, for example, an antibody or a tyrosine kinase inhibitor (TKI). In variations of this embodiment, the EGFR inhibitor is for example, cetuximab or panitumumab; and tyrosine kinase inhibitor is an erlotinib or gefitinib.

In further variations of this embodiment, the method further comprises testing the patients' sample (or recommending that the patient's sample be tested) for one more of the following mutations: G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins; and if one or more of the mutations are present, administering to the patient an EGFR inhibitor, including, for example, an antibody or a tyrosine kinase inhibitor (TKI).

Example 1

Identifying the Mutation in Lung Cancer Patient Samples

Tissue samples were obtained from lung cancer (NSCLC) patients. The biopsy samples were preserved as formalin-fixed, paraffin embedded tissue (FFPET). Nucleic acids were isolated from the samples and subjected to direct sequencing on the Illumina MISEQ™ Genome Sequencer (Illumina, Inc., San Diego, Calif.).

The 2257-2277>GCC mutation (as a combination of 2257-2262 del and 2266-2277 del) was detected in the sample E10. The mutation was detected in 9234 out of 17570 sequence reads (52.56%). Heterogeneity of the sequence reads is believed to stem from genetic heterogeneity of the tumor as well as the presence of non-tumor cells in the biopsy sample.

While the invention has been described in detail with reference to specific examples, it will be apparent to one skilled in the art that various modifications can be made within the scope of this invention. Thus the scope of the invention should not be limited by the examples described herein, but by the claims presented below.

We claim:

1. A method of treating a patient having a tumor possibly harboring cells with a mutation in the epidermal growth factor receptor (EGFR) gene, comprising:
   (a) testing the patient's sample for the presence of the mutated EGFR gene characterized by the mutation 2257-2277>GCC, or mutation 2257-2262 del, or mutation 2266-2277 del in SEQ ID NO: 1;
   (b) detecting in the sample the presence of the mutated EGFR gene characterized by the mutation 2257-2277>GCC, or mutation 2257-2262 del, or mutation 2266-2277 del in SEQ ID NO: 1; and
   (c) administering to the patient an EGFR inhibitor compound.

2. The method of claim 1, wherein the EGFR inhibitor compound is cetuximab, panitumumab, erlotinib or gefitinib.

3. The method of claim 1, further comprising in step (a), testing the patient's sample for the presence of the mutated EGFR gene characterized by one or more of the mutations G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-1759 del T ins, S752-1759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins.

4. The method of claim 3 wherein one or more mutations are detected by DNA sequencing.

5. A method of detecting mutation 2257-2277>GCC or mutation 2257-2262 del, or mutation 2266-2277 del in the human EGFR gene comprising carrying out allele-specific PCR on a patient sample with an allele specific oligonucleotide.

6. The method of claim 5, further comprising testing the patient sample for the presence of the mutated EGFR gene characterized by one or more of the mutations G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-1759 del T ins, S752-1759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins.

7. The method of claim 6, further comprising detecting mutation 2257-2277>GCC or mutation 2257-2262 del, or mutation 2266-2277 del in the human EGFR gene and administering an EGFR inhibitor compound to the patient.

8. A method of detecting mutation 2257-2277>GCC or mutation 2257-2262 del, or mutation 2266-2277 del in the human EGFR gene comprising carrying out DNA sequencing on a patient sample with an allele specific oligonucleotide.

9. The method of claim 8, further comprising testing the patient sample for the presence of the mutated EGFR gene characterized by one or more of the mutations G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-1759 del T ins, S752-1759 del, P753-K757 del, M766-A767 del AI ins, S768-V769 del SVA ins, G779S, P848L, G857V, L858R, L861Q, L883S, D896Y, 2236_2248>ACCC, 2237_2244>CGCCC, 2252_2277>AC, 2240-2264>CGAAAGA, 2239_2240 TT>CC, 2264 C>A and E746-A750 del AP ins.

10. The method of claim 8, further comprising detecting mutation 2257-2277>GCC or mutation 2257-2262 del, or mutation 2266-2277 del in the human EGFR gene and administering an EGFR inhibitor compound to the patient.

\* \* \* \* \*

SEQUENCE LISTING

```
<160> NUMBER OF SEQ ID NOS: 3

<210> SEQ ID NO 1
<211> LENGTH: 3633
<212> TYPE: DNA
<213> ORGANISM: Homo sapiens

<400> SEQUENCE: 1
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca ccagtgtgc tgcaggctgc    720
```

```
acaggccccc gggagagcga ctgcctggtc tgccgcaaat tccgagacga agccacgtgc    780
aaggacacct gccccccact catgctctac aaccccacca cgtaccagat ggatgtgaac    840
cccgagggca aatacagctt tggtgccacc tgcgtgaaga agtgtccccg taattatgtg    900
gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg gctgctgggg cccggagccc   1560
agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgcccggc aggagtcatg   1800
ggagaaaaca caccctggt ctggaagtac gcagacgccg ccatgtgtg ccacctgtgc    1860
catccaaact gcacctacgg atgcactggg ccaggtcttg aaggctgtcc aacgaatggg   1920
cctaagatcc cgtccatcgc cactgggatg gtggggccc tcctcttgct gctggtggtg    1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta aagggactc tggatcccag aaggtgagaa agttaaaatt    2220
cccgtcgcta tcaaggaatt aagagaagca acatctccga aagccaacaa ggaaatcctc   2280
gatgaagcct acgtgatggc cagcgtggac aaccccacg tgtgccgcct gctgggcatc    2340
tgcctcacct ccaccgtgca gctcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gctggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgactg tttgggagtt gatgaccttt ggatccaagc catatgacgg aatccctgcc   2760
agcgagatct cctccatcct ggagaaagga gaacgcctcc ctcagccacc catatgtacc   2820
atcgatgtct acatgatcat ggtcaagtgc tggatgatag acgcagatag tcgcccaaag   2880
ttccgtgagt tgatcatcga attctccaaa atggcccgag accccagcg ctaccttgtc    2940
attcaggggg atgaaagaat gcatttgcca agtcctacag actccaactt ctaccgtgcc   3000
ctgatggatg aagaagacat ggacgacgtg gtggatgccg acgagtacct catcccacag   3060
cagggcttct tcagcagccc ctccacgtca cggactcccc tcctgagctc tctgagtgca   3120
```

-continued

```
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                3633
```

<210> SEQ ID NO 2
<211> LENGTH: 31
<212> TYPE: DNA
<213> ORGANISM: Homo sapiens

<400> SEQUENCE: 2
aacatctccg aaagccaaca aggaaatcct c    31

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aacatctgcc ctc    13